(12) United States Patent
'T Hooft et al.

(10) Patent No.: US 7,489,405 B2
(45) Date of Patent: Feb. 10, 2009

(54) OPTICAL COHERENCE TOMOGRAPHY

(75) Inventors: Gert Wim 'T Hooft, Eindhoven (NL);
Egbert Lenderink, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 276 days.

(21) Appl. No.: 10/523,046

(22) PCT Filed: Jul. 16, 2003

(86) PCT No.: PCT/IB03/03228

§ 371 (c)(1),
(2), (4) Date: Feb. 2, 2005

(87) PCT Pub. No.: WO2004/015402

PCT Pub. Date: Feb. 19, 2004

(65) Prior Publication Data

US 2005/0232536 A1    Oct. 20, 2005

(30) Foreign Application Priority Data

Aug. 7, 2002  (EP)  ................... 02078265

(51) Int. Cl.
*G01B 9/02* (2006.01)

(52) U.S. Cl. .................................... 356/497

(58) Field of Classification Search .................. 356/479, 356/497
See application file for complete search history.

(56) References Cited

U.S. PATENT DOCUMENTS

| 5,365,335 | A | * | 11/1994 | Sorin | 356/479 |
| 5,530,709 | A | * | 6/1996 | Waarts et al. | 372/6 |
| 6,160,826 | A | * | 12/2000 | Swanson et al. | 372/20 |
| 7,106,762 | B1 | * | 9/2006 | Jiang et al. | 372/6 |

OTHER PUBLICATIONS

R. C. Sharp; "190-FS Passively Mode-Locked Thulium Laser With a Low Threshold", Optics Letters, Optical Society of America, Washington, vol. 21, No. 12.
'Optical coherence tomography', David Huang et al., in Science 254(1991)1178-1181.
'Optical coherence tomographicn imaging of human tissue at 1.55μm and 1.81μm using Er- and Tm-doped fiber sources' by B.E. Bouma et al, in J. Biomedical Optics 3(1998)76-79.

* cited by examiner

*Primary Examiner*—Hwa (Andrew) S Lee

(57) ABSTRACT

An optical coherence tomography system includes an optical source has an emission wavelength in the range of 1.6 μm to 2.0 μm, in particular having an infrared emission predominantly at a wavelength of 1.8 μm associated with a transition between an upper energy level and a lower energy level and the optical source comprises an excitation system which generates stimulated emission from a pump level to the upper energy level. The optical source may include a Tm-doped fiber in an optical cavity.

7 Claims, 2 Drawing Sheets

OPTICAL COHERENCE TOMOGRAPHY

Figure 1:
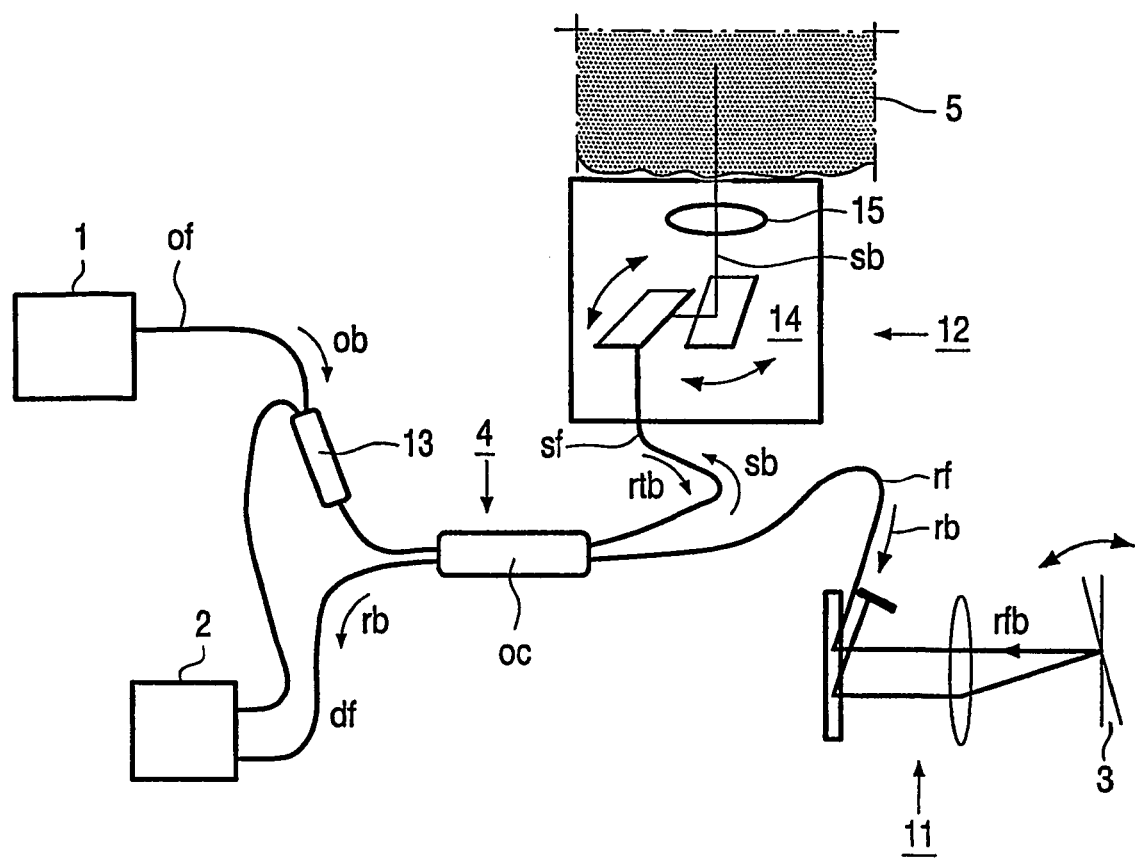

The invention pertains to an optical coherence tomography system comprising
- an optical source to emit an optical beam
- a sample space
- a photodetector
- an interferometer set-up including
  - a reference reflector and
  - a beam splitter-combination arrangement to
    - split the optical beam into a reference beam to the reference reflector and a sample beam to the sample space and to
    - combine a reflected beam from the reference reflector with a returning beam from the sample space on the photodetector.

Such an optical coherence tomography system is known from the paper '*Optical coherence tomography*' in Science 254(1991)1178-1181.

The known optical coherence tomography system uses low-coherence interferometry to produce a two-dimensional image of optical scattering from internal tissue microstructures. Low-coherence interferometry, notably reflectrometry, can be performed with continuous-wave light without the need for ultrashort laser pulses. In low-coherence reflectometry the coherence property of the light returning from a sample that is placed in the sample space provides information on the time-of-flight delay from reflective boundaries and backscattering sites in the sample. Optical coherence tomography's resolution is limited only by the coherence length of the optical source. The known optical coherence tomography system comprises a fibre optic Michelson interferometer which is illuminated by low-coherence light from a super luminescent diode (SLD) which operates at a wavelength of 830 nm and at an optical power of 20 µW. To acquire data for the two-dimensional image, a series of longitudinal scans are performed with the sample beam position translated laterally between longitudinal scans.

The cited paper mentions a few aspects of optical coherence tomography which can be further improved, namely employ angular alignment of the optical coherence tomography system to achieve near normal incidence of the sample beam in order to measure specular surfaces, use large numerical apertures in the interferometer set up. Further the cited reference notes that speckle noise adversely affects detection of subtle differences in tissue backscattering properties and multiply scattered light form echoes which limit the depth range of optical coherence tomography in situations where scattering predominates over absorption.

An object of the invention is to provide an optical coherence tomography system which is able to reach a greater penetration depth range.

This object is achieved by an optical coherence tomographry system according to the invention wherein
  the optical source has an emission wavelength in the range of 1.6 µm to 2.0 µm, in particular having an infrared emission predominantly at a wavelength of 1.8 µm associated with a transition between an upper energy level and a lower energy level and
  the optical source comprises an excitation system which generates stimulated emission from a pump level to the upper energy level.

Accordingly, the optical coherence tomography system according to the invention operates at a wavelength at which tissue to be examined has both low optical absorption and low scattering in the tissue containing blood vessels. In particular the scattering reduces for higher wavelengths larger than 1.6 µm and absorption mainly by water in the tissue increases for wavelengths larger than 1.6 µm, but the absorption remains at a moderate level for wavelengths less than 2.0 µm such that a sufficient number of photons is able to penetrate into the tissue and return to the photodetector to form a useful detection signal. Furthermore in the range of wavelengths from 1.6 µm to 2.0 µm there is a substantial scattering at tissue transitions. Further, the range of 1.6-2.0 µm lies just above the absorption band of major blood components such as haemoglobin and oxyhaemoglobin. In particular at a wavelength of 1.8 µm there occurs a local minimum in the absorption by water as a function of wavelength. Hence, particularly good results for the penetration depth and signal level of the detection signal formed by the photodetector are achieved at the wavelength of 1.8 µm. Further, the range of wavelengths of 1.6-2.0 µm is advantageous when optical coherence tomography imaging is applied from the inside of a blood vessel to examine the vessel wall. The relatively low absorption of the sample beam and returning beam by the blood in the vessel allows these beams to pass through the blood in the vessel with low attenuation so that a useful signal-to-noise ratio is achieved for the detection signal.

Optical coherence tomography imaging with a source wavelength near 1.8 µm was proposed per se in the paper '*Optical coherence tomographicn imaging of human tissue at 1.55 µm and 1.81 µm using Er- and Tm-doped fiber sources*' by B. E. Bouma et al, in J. Biomedical Optics 3(1998)76-79. However, the pumping efficiency of the known Tm-doped fibre source is very inefficient. Hence, in order to achieve an adequate signal-to-background and signal-to-noise ratio for the detection signal, the known Tm-doped fibre source should be pumped at a pump level that is extremely difficult to achieve. Further, increasing the Tm-concentration would not lead to an increase of the intensity of the output light at 1.8 µm due to increased cross relaxation between neighbouring Tm-atoms.

According to the invention, the pumping efficiency is enhanced by enabling stimulated emission to the upper level so that the population of the upper level is enhanced. The stimulated emission from the pump level to the upper level is achieved by the excitation system. To this end the excitation system is arranged to reduce losses of the radiation associated with the transition between the pump level and the upper level. Notably, these reduced losses lower the lasing threshold of transition between the pump level and the upper level. The excitation system is arranged to obtain reduction of these losses are achieved by influencing a combination of various circumstances. Cavity losses of the Tm-fibre for the transitions from the pump level to the upper level are lowered e.g. by providing cavity reflectors having a high reflectivity for the radiation associated with transitions from the pump level to the upper level. Further, multiphonon emission is influenced by the surroundings of the Tm-atoms in the fibre glass. Too high a maximum phonon energy causes unfavourable competition of the radiative transition between the upper and lower levels with multiphonon emission from the upper level. On the other hand too low a maximum phonon energy leads to a low pumping efficiency because multiphonon emission assists the transitions from the pump level to the upper level, which leads to sufficient population of the upper level from the pump level. According to the invention, the excitation system involves a combination of the cavity and fibre-type glass which has a lasing threshold between the pump level and upper level which enables the stimulated emission which greatly enhances the pump efficiency.

A particularly suitable low-coherence light source which produces an optical beam at a wavelength of about 1.8 µm is formed according to the invention by a Tm-doped (Thulium) fibre that is placed in an optical cavity formed by cavity reflectors. The optical (infrared) radiation at the wavelength of 1.81 μm stems from the $^3F_4 \to {}^3H_6$ upper to lower level transition in the Tm atoms in the fibre. This transition can be optically pumped by pump radiation of a wavelength of about 790 nm which excites the $^3H_6$ ground state to the $^3H_4$ excited level, i.e. the pump level which relaxes partly to the $^3F_4$ upper level.

Preferably the cavity reflectors are anti-reflex coated for a wavelength range of 760-810 nm to reduce stimulated emission around 790 nm due to relaxing of the $^3H_4$ excited level to the ground state. Hence, emission highly coherent (infrared) laser light at 790 nm is substantially avoided.

Preferably, the cavity reflectors have a high-reflection coating of a reflectivity of typically more than 0.99 for wavelengths in the range of 2.2-2.4 μm. Hence, the optical pumping efficiency of the $^3F_4$ level is enhanced by involving stimulated emission at typically 2.3 μm of the $^3H_4 \to {}^3H_5$ transition. The $^3H_5$ level has a relatively short lifetime of about 10 μs owing to non-radiative transitions to the $^3F_4$ level.

Preferably, the cavity reflectors have a high-reflectivity of typically more than 0.99 in the wavelength range of 1.40-1.55 μm. Hence the transition $^3H_4 \to {}^3F_4$ involves stimulated emission thus enhancing the pumping efficiency of the $^3F_4$-level.

Preferably, the optical cavity has reflectivities for wavelengths in the range 1.6-2.0 μm of less than 0.04, so that lasing action between the upper and lower levels is avoided and the coherence length of the output light in the range of 1.6-2.0 μm is low. Thus, in particular laser action at the wavelength of 1.8 μm is avoided and emission of low-coherence infrared light at 1.8 μm is achieved. Typically a bandwidth of about 200 nm is achieved which corresponds to a coherence length $$l_{coh} = \frac{\lambda^2}{\Delta\lambda} \approx 16 \ \mu m.$$

The invention further pertains to an optical amplifier. The optical amplifier of the invention is advantageously employed as a broad-band amplifier in the L-band for example in the wavelength range of 1570-1610 nm of optical telecommunication networks.

The invention further pertains to a Tm-doped optical fiber. The double cladding layer provides extra guiding of the pump light. Hence, the pump light source, for example a semiconductor laser that emits predominantly at the pump wavelength in the region of 790 nm needs not be accurately focused to a spot size of about the core size of the fiber, but a substantially larger than the core size. Further the double cladding allows the Tm-doped optical fiber to be optically pumped in a multimode fashion, which the output radiation, or the amplified output radiation remains single mode.

Figure 2:
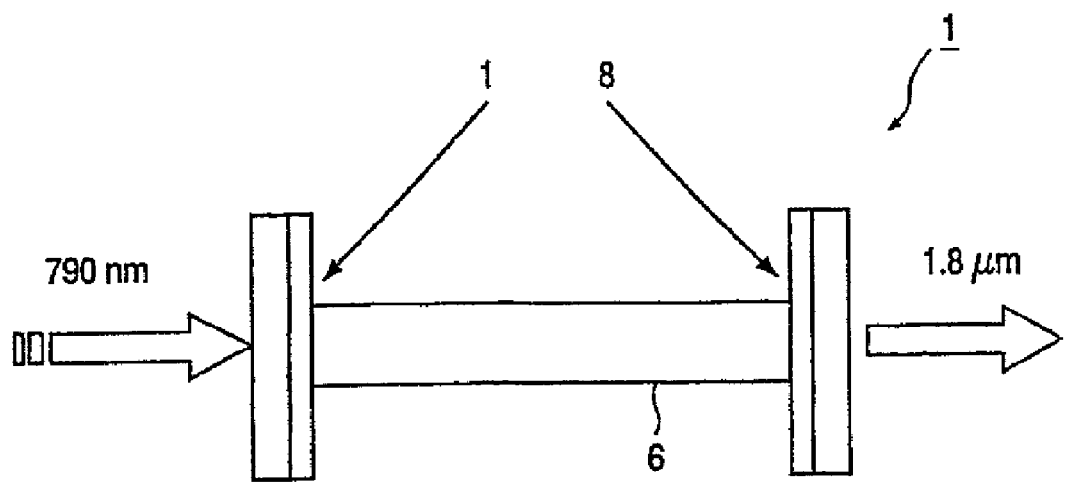
Figure 3:
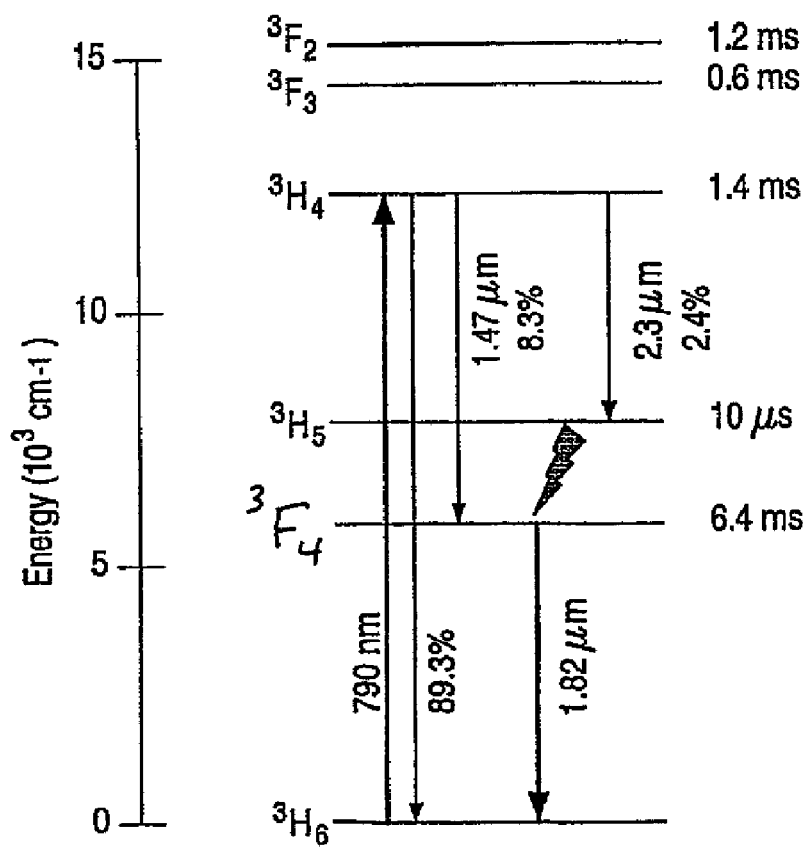

These and other aspects of the invention will be elucidated with reference to the embodiments described hereinafter and with reference to the accompanying drawing wherein FIG. 1 shows a schematic representation of an optical coherence tomography system according to the invention;

FIG. 2 shows a schematic representation the optical source used in the optical coherence tomography system of the invention and FIG. 3 shows the energy level diagram of Thulium.

FIG. 1 shows a schematic representation of an optical coherence tomography system according to the invention. The optical coherence tomography system comprises the optical source 1 which emits the optical beam (ob) into an optical fibre (of). The optical beam propagates from an exit face of the of optical source through the optical fibre (of). The beam splitter-combination arrangement 4 is implemented in the form of a 2×2 fibre coupler(oc). The 2×2 fibre coupler (oc) divides the optical beam (ob) into the reference beam (rb) and the sample beam (sb). The reference beam passes through a reference fibre (rf) to a fast scanning delay line 11 which incorporates the reference reflector 3. The sample beam passes through a sample fibre (sf) to the sample space 5 via a measuring head 12. The reflected beam (rfb) from the reference reflector 3 and the returning beam (rtb) return to the beam splitter-combination arrangement 4 which combines the reflected beam (rfb) with the returning beam (rtb) and the combined beam are supplied to the photodetector 2 by way of a detection fibre (df). Part of the radiation that passes from the beam splitter-combination arrangement 4 to the optical source 1 is coupled out by way of a second 2×2 fibre coupler 13 to a second port of the photodetector to perform so-called balanced detection so as to reduce noise in the photodetector output signal. Balanced detection is performed by automatic scaling and subtraction of the photodetector signal and a reference signal. The photodetector signal is derived from the intensity of the combined beam supplied by the detection fibre and the reference signal is taken from the second 2×2 fibre coupler. Thus common noise, notable generated in the optical source is rejected.

The reference fibre and the measuring head with the reference reflector form a reference arm of the interferometer set up. The sample fibre with the measuring head form an object arm of the interferometer set up. The optical path-length of the reference arm is adjustable by tilting the reference mirror 3 in the fast scanning delay line 11. Interference occurs at the photodetector, positive interference is observed when both arms of the interferometer set up are equal in optical path-length. Thus, by setting the path-length of the reference arm one selects a narrow window inside the sample space, i.e. within the object to be examined, from which a photodetector signal with a substantial signal level is obtained. The interferometer set up is advantageously constructed in fibre optic form as shown in FIG. 1, to avoid high sensitivity of alignment of the various optical components. The measuring head 12 includes scanning mirrors 14 and a focussing lens 15 to scan and focus the sample beam (sb) over the object to be examined.

FIG. 2 shows a schematic representation the optical source used in the optical coherence tomography system of the invention. The optical source for the optical coherence tomography system according to the invention comprises the Thulium-doped optical fibre 6 which is placed in the optical cavity formed by the cavity reflectors 7,8. There is an input cavity reflector 7 on which the pump light having a wavelength of about 790 nm is incident. There is an output cavity reflector from which the emission wavelength having its wavelength in the rage of 1.6-2.0 μm is emitted. A suitable material for the optical fibre is fluorozirconate glass, since it has a maximum phonon energy in a range in which on the one hand radiative radiation from the upper level to the lower level has a favourable branching ratio to the non-radiative losses and on the other hand pumping is sufficiently assisted.

In FIG. 3 the energy diagram of Tm is schematically shown as published by T. Schweizer, B. N. Samson, J. R. Hector, W. S. Brocklesby, D. W. Hewak, and D. N. Payne, in "Infrared emission and ion-ion interactions in thulium- and terbium-doped gallium lanthanum sulphide glass"; J Opt. Soc. Am. B 16, 308-316 (1999). The fluorescence of Tm at 1.8 μm stems from the $^3F_4 \to {}^3H_6$ transition. To pump the $^3F_4$ level, light with a wavelength around 800 nm is used, exciting the $^3H_4$ level, which relaxes radiatively as well as non-radiatively to the $^3H_5$ (2.3 µm) and $^3F_4$ (1.47 µm) level. Generally, the $^3H_5$ level has a relatively small lifetime around 10 µs, owing to non-radiative transitions to the $^3F_4$ level. Because of the high maximum phonon energy in silica glasses (~1150 cm$^{-1}$) the luminescence yield is limited by competition between multiphonon emission and radiative emission from the upper level. On the other hand, multiphonon emission is important in the pumping process because it provides the decay from the pump level, $^3H_4$ to the upper level of the preferred luminescence, the $^3F_4$ level. Too low a phonon energy can result in a low pumping efficiency. An example of this effect is provided by the $^3F_4 \rightarrow ^3H_6$ transition in Tm. In ZBLAN-glass with its maximum phonon energy of 590 cm$^{-1}$ the $^3F_4 \rightarrow ^3H_6$ transition has a high radiative quantum yield but is limited by a low pumping efficiency. The pumping efficiency of the $^3F_4$ level in the fluorozirconate host can be enhanced by using a high dopant concentration (>1%). At higher dopant levels a cross-relaxation mechanism ($^3H_4, ^3H_6$)→($^3H^4, ^3F_4$) between neighbouring Tm$^{3+}$-ions becomes efficient which gives rise to two ions being excited to the $^3F_4$ upper level for each pump photon absorbed. One excited ion interacts with an ion in the ground state, and both end up in the $^3F_4$ state. Consequently, the cross-relaxation process provides an additional decay channel for the $^3H_4$ state which causes so-called concentration quenching and thereby shortening its lifetime.

According to the invention the pumping efficiency of the $^3F_4$ level is enhanced by involving stimulated emission of the $^3H_4 \rightarrow ^3H_5$ transition at 2.3 µm and the $^3H_4 \rightarrow ^3F_4$ transition at 1.47 µm. To this end the fibre is butted with two mirrors which form the cavity reflectors with special coatings which obey the following criteria:

1. At low excitations the branching ratios of the $^3H_4$ level are such that 89% relaxes directly back to the ground state. To reduce stimulated emission of this transition around 800 nm the mirrors should have an anti-reflection coating for 760-810 nm.
2. To increase the branching ratio of 2.4% to the $^3H_5$ level the mirrors should have a high reflection coating (>99%) in the wavelength range 2.2-2.4 µm. Making the fibre light source of fluorozirconate glass the phonon energies are large enough to efficiently relaxing the $^3H_5$ level to the $^3F_4$ level via a multiphonon process.
3. To increase the branching ratio of 8.3% to the $^3F_4$ level the mirrors should have a high reflection coating (>99%) in the wavelength range 1.40-1.55 µm.
4. To increase the amount of amplified spontaneous emission around 1.8 µm, but at the same time prevent the device from laser action, thereby leaving the emission spectrum as broad as possible, the input mirror should have a high reflection coefficient (>99%) and the output mirror a low reflection coefficient (<1%) for the wavelength range 1.6-2.0 µm.
   Alternatively, by a small design modification, i.e. both mirrors should have an anti-reflection coating at 1.8 µm, the light source can be used as a broadband amplifier in the L-band of optical telecommunication networks.

To maintain a good focusability on the one hand, i.e. a limited amount of spatial modes in the wavelength range around 1.8 µm, the cut-off wavelength should not be chosen to high. On the other hand pumping at 800 nm with semiconductor laser diodes demands reasonable core sizes. A cut-off wavelength just below 1.8 µm seems to be an attractive alternative. Furthermore, a double cladding layer provides extra guiding of the pump light, which is attractive when the semiconductor laser light can not be focused to a spot size roughly equalling the core size of the fibre (7-10 µm).

The length of the fibre and the concentration of the Tm are related. The absorption cross section of Tm at 790 nm is $3 \times 10^{-21}$ cm$^2$. A concentration of 1% corresponds to $8 \times 10^{19}$ ions cm$^{-3}$, resulting in a absorption of 0.24 cm$^{-1}$, i.e. ~100 dB/m. Usually, the pump light will be guided by the first cladding with a diameter of 125 mm. Hence, the effective attenuation of the pump laser light will be far less 5 say 2-5 dB/m. Consequently, a fibre length of 0.5-1 m will suffice at a dopant concentration of 1%.

The invention claimed is:

1. An optical coherence tomography system comprising:
   an optical source to emit an optical beam;
   a sample space;
   a photodetector;
   an interferometer set-up including
      a reference reflector, and
      a beam splitter-combination arrangement to
         split, the optical beam into a reference beam to the reference reflector and a sample beam to the sample space, and to
         combine a reflected beam from the reference reflector with a returning beam from the sample space to form
   a combined beam, and provide the combined beam to a first port
   of the photodetector, and
   a further beam splitter which receives part of a radiation from the beam splitter-combination arrangement and couples out a reference signal to a second port of the photodetector, wherein the photodetector scales and subtracts the combined signal and the reference signal to form an output photodetector signal having a reduced noise for output from the photodetector;
   wherein
      the optical source has an emission wavelength in the range of 1.6 µm to 2.0 µm, associated with a transition between an upper energy level and a lower energy level, and
      the optical source comprises an excitation system which generates stimulated emission from a pump level to the upper energy level.

2. The optical coherence tomography system as claimed in claim 1, wherein the optical source includes a Tm-doped fiber placed in an optical cavity of cavity reflectors facing one another.

3. The optical coherence tomography system as claimed in claim 2, wherein the cavity reflectors are anti-reflex coated for a wavelength range of 760 nm to 810 nm.

4. The optical coherence tomography system as claimed in claim 2, wherein the cavity reflectors have a high-reflectivity for the wavelength range 2.2 µm to 2.4 µm.

5. The optical coherence tomography system as claimed in claim 2, wherein the cavity reflectors have a high-reflectivity for the wavelength range 2.2 µm to 2.4 µm and/or for the wavelength range 1.40 µm to 1.5 µm.

6. The optical coherence tomography system as claimed in claim 2, wherein the optical cavity has reflectivities less than 0.04 for the wavelength range of 1.6-2.0 µm.

7. The optical coherence tomography system as claimed in claim 6, wherein
   an input cavity reflector has a high reflectivity for the wavelength range 1.6 µm to 2.0 µm; and
   an output cavity reflector has a low-reflectivity for the wavelength range 1.6 µm to 2.0 µm.

* * * * *